United States Patent
Ashby et al.

[11] Patent Number: 5,928,286
[45] Date of Patent: Jul. 27, 1999

[54] TIBIAL ELEMENT FOR A REPLACEMENT KNEE PROSTHESIS

[75] Inventors: Alan Ashby, Lymington, United Kingdom; Paul F. Dorrell, Castleconnell, Ireland

[73] Assignee: Howmedica International Inc., Ireland

[21] Appl. No.: 08/864,021

[22] Filed: May 27, 1997

[30] Foreign Application Priority Data

May 28, 1996 [GB] United Kingdom .................. 9611059

[51] Int. Cl.⁶ .................................................. A61F 2/38
[52] U.S. Cl. ................................................................ 623/20
[58] Field of Search ................................ 623/20, 18, 16

[56] References Cited

U.S. PATENT DOCUMENTS

| | | | |
|---|---|---|---|
| 4,711,639 | 12/1987 | Grundei | 623/20 |
| 4,936,853 | 6/1990 | Fabian et al. | 623/20 |
| 5,071,438 | 12/1991 | Jones et al. | 623/20 |
| 5,282,868 | 2/1994 | Bahler | 623/20 |
| 5,395,401 | 3/1995 | Bahler | 623/20 |
| 5,413,604 | 5/1995 | Hodge | 623/20 |

FOREIGN PATENT DOCUMENTS

| | | | |
|---|---|---|---|
| 0552950 A1 | 7/1993 | European Pat. Off. | |
| 0 582 514 A1 | 2/1994 | European Pat. Off. | 623/20 |
| 0592750 A1 | 4/1994 | European Pat. Off. | |
| 0634155 A2 | 1/1995 | European Pat. Off. | |
| 0634156 A2 | 1/1995 | European Pat. Off. | |
| 0678286 A1 | 10/1995 | European Pat. Off. | |
| 2 663 536 A1 | 12/1991 | France | 623/20 |
| 2 702 651 A1 | 9/1994 | France | 623/20 |
| 39 22 294 C1 | 1/1991 | Germany | 623/20 |
| 43 08 563 A1 | 9/1994 | Germany | 623/20 |
| 2280375 | 2/1995 | United Kingdom | |
| 2280376 | 2/1995 | United Kingdom | |
| 95/17860 | 7/1995 | WIPO | 623/20 |
| 95/25484 | 9/1995 | WIPO | 623/20 |
| WO9638103 | 12/1996 | WIPO | |

*Primary Examiner*—David H. Willse
*Attorney, Agent, or Firm*—Lerner, David, Littenberg, Krumholz & Mentlik

[57] ABSTRACT

A tibial element for a replacement knee prosthesis has a tibial tray, fastening connector for securing an attachment element to the lower part of the tray, and also provided with independently operable securing boss at its upper end which engage a cooperating construction on a bearing component to secure the bearing component to the upper part thereof. The fastening connector allows for a stronger construction than the previous arrangements and it also allows for a convenient modular construction which will allow a standard modular tray to be employed with various types of bearing construction, for example, a fixed component or a sliding component.

12 Claims, 9 Drawing Sheets

TIBIAL ELEMENT FOR A REPLACEMENT KNEE PROSTHESIS

BACKGROUND OF THE INVENTION

1. Field of the Invention

This invention relates to a tibial element for a replacement knee prosthesis of the kind comprising a tibial tray provided with one or more bearing components.

2. Description of the Prior Art

It is known to provide a tibial tray with an attachment element, for example a stem, which can be selected and fitted by the operating surgeon. Thus, trays can be provided with a variety of stems of different lengths and construction which can be used in accordance with the surgical and medical requirements at the time the prosthesis is fitted.

In the construction showed in the Applicants' U.S. application Ser. No. 5,413,605, the stem is held to the tray by means of a tapered spigot and socket connection that is locked in place by a fixing screw 60. The bearing component is held in position by a capture system employing a number of small catches. This capture arrangement entails a number of accurately made features and the present invention is intended to provide a simplified construction that will not only be more effective but easier to manufacture.

SUMMARY OF THE INVENTION

According to the present invention a tibial element for a replacement knee prosthesis comprises a tibial tray, fastening means for securing an attachment element to the lower part of said tray, and also provided with independently operable securing means at its upper end which engage a cooperating construction on a bearing component to secure the bearing component to the upper part thereof.

Thus, with the present arrangement the fastening means allows for a stronger construction than the previous arrangements and it also allows for a convenient modular construction that will allow a standard modular tray to be employed with various types of bearing construction, for example a fixed component or a sliding component.

Preferably the independently operable securing means are releasable, thus allowing the bearing component to be removed and replaced without disturbing the connection of the tibial element to the bone.

As mentioned above the bearing component can be arranged to slide in relation to the tray when secured or alternatively it can be fixed in position in relation to the tray.

The fastening means can be provided with a boss at its upper end which is shaped to cooperate with the cooperating retaining construction on the bearing component.

Such a boss can have a projecting flange shaped to engage a securing flange provided on the bearing component.

Two bearing components can be provided, each component having a cooperating construction which engages the independently operable securing means and if desired, each bearing component can be independently engageable with the securing means.

In a preferred construction the bearing component is a snap fit onto the independently operable securing means provided on the fastening means to relatively secure said bearing component.

The invention is intended to provide good post operative stability of the joint, provide a low sensitivity to surgical technique and soft tissue quality and provide mechanisms to avoid the likelihood of insert dislocation and other bearing damage.

The tray can be standard for both left and right knees and the bearing components handed. With this arrangement the tray can be substantially symmetrical about a vertical axis.

These and other objects and advantages of the present invention will become apparent from the following description of the accompanying drawings, which disclose several embodiments of the invention. It is to be understood that the drawings are to be used for the purposes of illustration only and not as a definition of the invention.

BRIEF DESCRIPTION OF THE DRAWINGS

In the drawings, wherein similar reference characters denote similar elements throughout the several views.

DESCRIPTION OF THE PREFERRED EMBODIMENT

Figure 1:
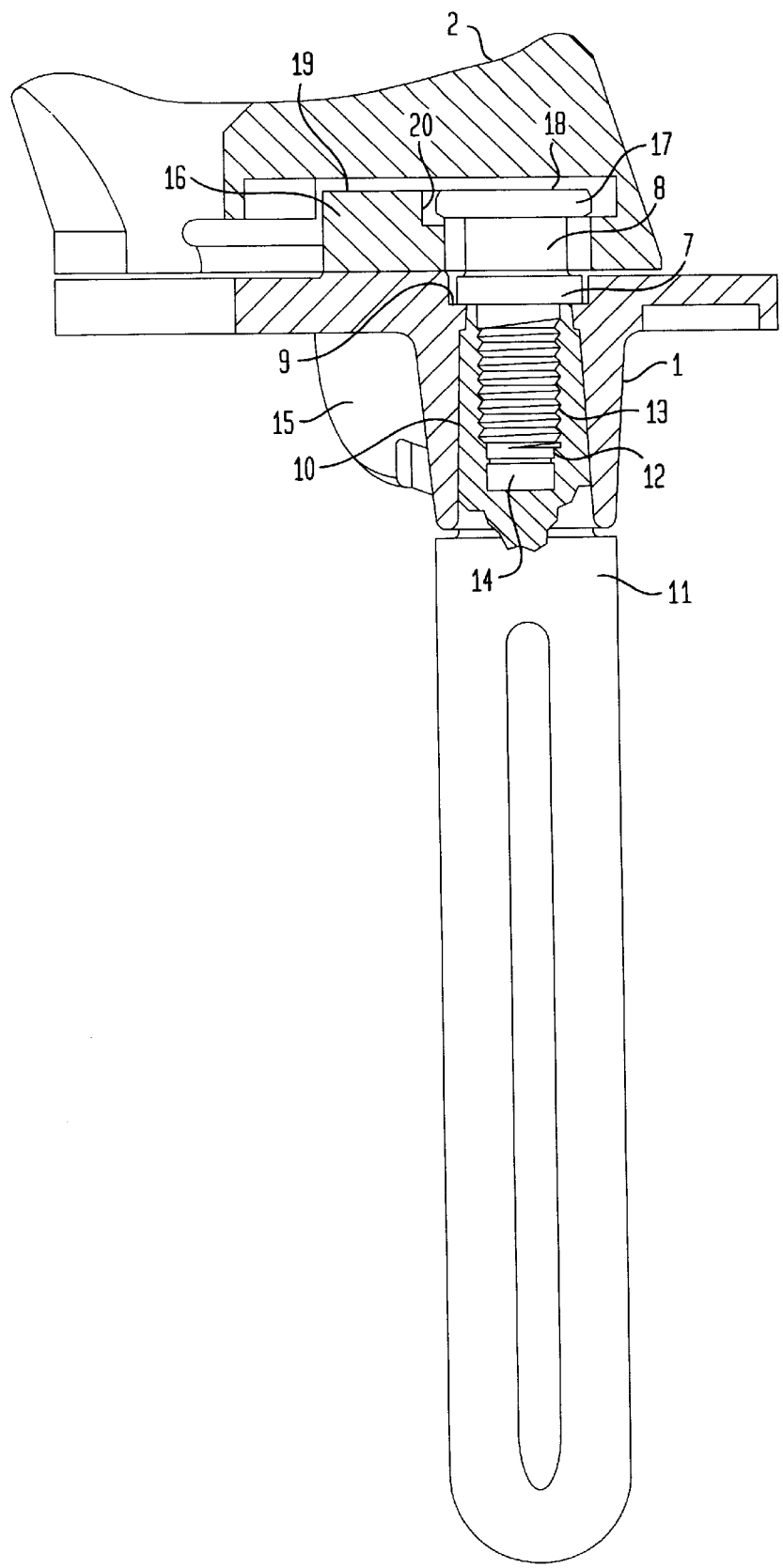
FIG. 1 is a part cross-sectional side elevation of a tibial element according to the present invention.
Figure 2:
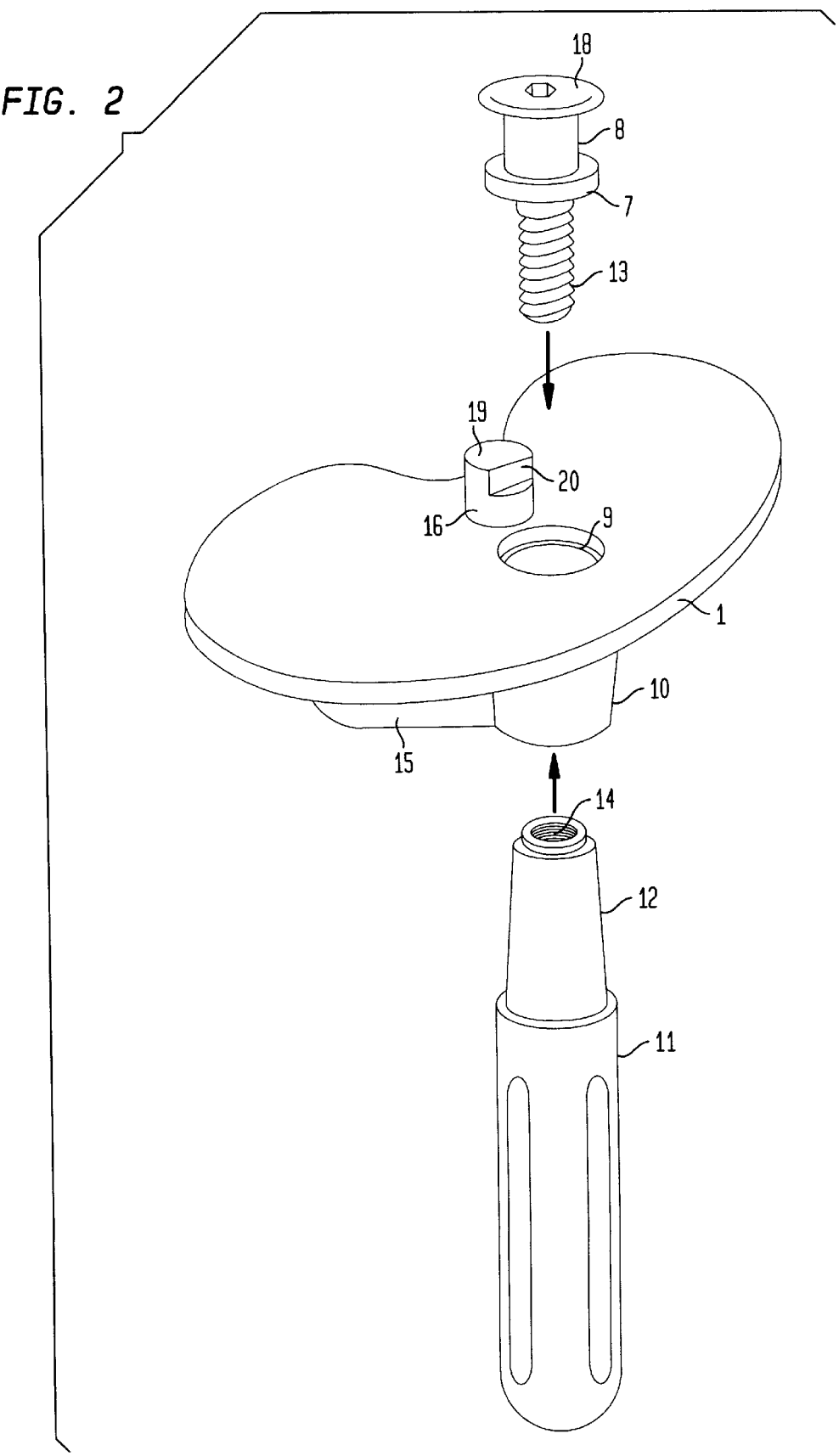
FIG. 2 is an exploded view of the construction shown in FIG. 1 with the bearing component removed.
Figure 4:
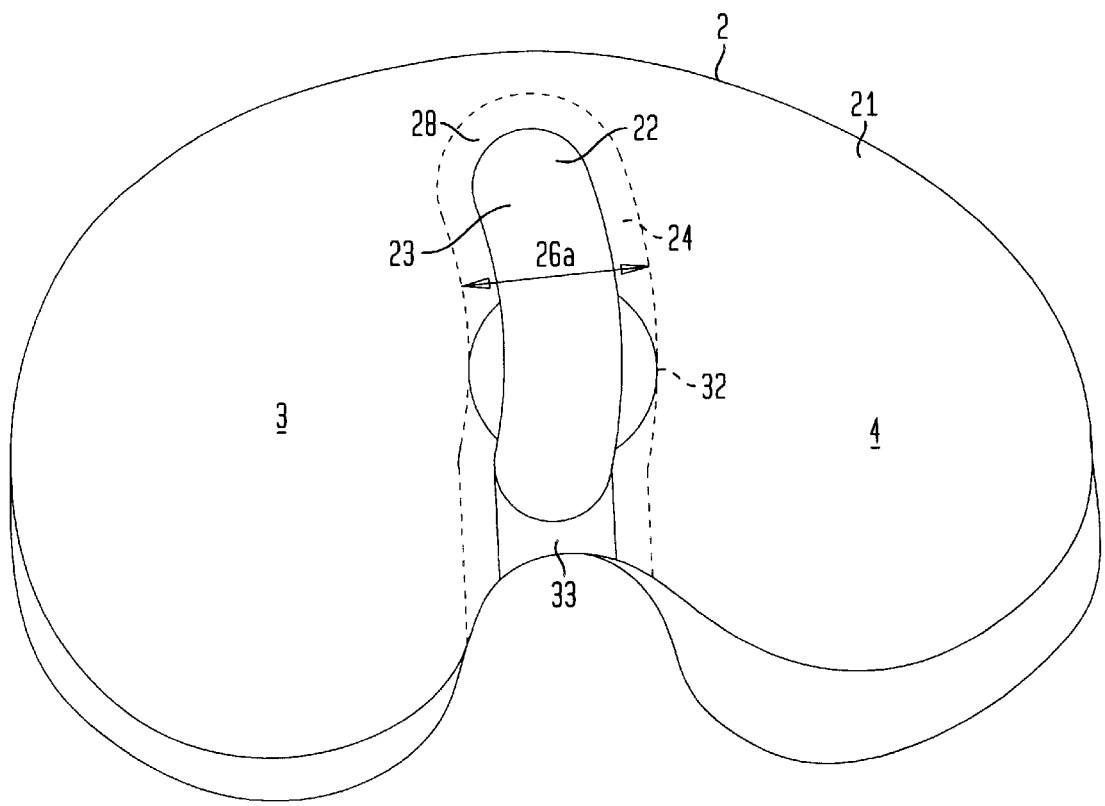
FIG. 4 is a plan view from below of the bearing component shown in FIG. 3.

As shown in FIGS. 1 and 2 a tibial element for a replacement knee prosthesis comprises a tibial tray 1 on which is carried a bearing component 2 having medial and lateral compartments respectively 3 and 4 and which are best shown in FIG. 4. The upper surfaces of the compartments 3 and 4 are shaped to provide bearing surfaces 5 and 6. The tray itself is standard for both left and right knees and is substantially symmetrical about a vertical axis.

Fastening means are provided which act to secure an attachment element in the form of a stem to the lower part of the tray. These are in the form of a screw 7 having an enlarged boss shaped head 8. The lower part of the boss bears against a flange 9 on the tray and enters a tapered opening 10 where it acts to retain a stem 11 which has a cooperating tapered spigot 12 by engaging a screw thread 13 in a socket 14.

The lower surface of the tray can be provided with shaped engagement features 15 intended for engagement with the proximal sub-condylar area of the tibia of the patient and the general construction of the connection between the tray and the stem can, for example, be as set forth in the Applicant's U.S. Pat. No. 5,413,605.

The upper surface of the tray 1 is provided with a central abutment 16, the function of which will be defined hereunder. It will be seen that the boss 8 of the screw 7 projects upwardly and the upper end is provided with a flange 17. When in position the upper surface 18 of the boss 8 is substantially horizontal in line with the upper surface 19 of the abutment 16. As is most clearly shown in FIGS. 1 and 2, the side of the abutment 16 adjacent the boss 8 is cut away to provide a recess 20 within which the flange 17 of the boss 8 is located when the screw 7 is in position.

Figure 3:
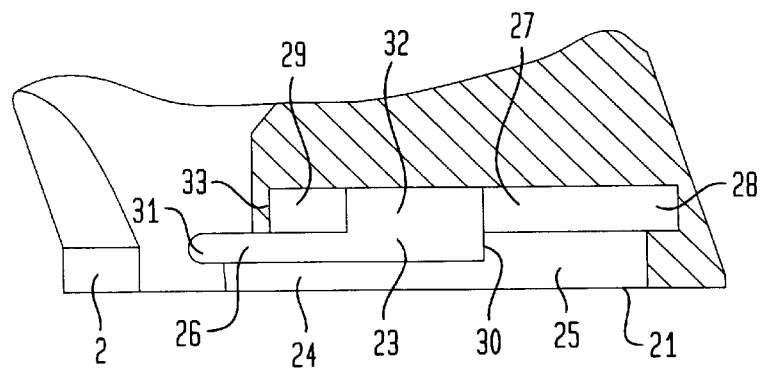
FIG. 3 is a cross-sectional side elevation of the bearing component shown in FIG. 1.

As shown in FIGS. 3 and 4, the bearing component 2 has medial 3 and lateral 4 compartments and can be made from any suitable bearing material, for example, ultra high molecular weight polyethylene. The lower surface 21 of the bearing component 2 is shaped to provide a curved track 22 which is most clearly shown in FIG. 4. This curved track 22 is provided by a recess 23 which is formed with a peripheral inwardly protruding securing flange 24 around its edges. At the anterior end of the recess 23 the flange is deeper and is indicated by reference numeral 25.

Above the flange 24 the recess 23 is shaped to provide two horizontally extending grooves, the lower groove being indicated by reference numeral 26 and an upper groove 27 above the deeper portion 25 of the flange 24. The anterior end of the upper groove 27 is in the form of a radiused portion 28 so that the groove is closed at this end. The posterior end of the upper groove also has a radiused portion 29.

The posterior ends 31 of the lower groove 26 are open and emerge out of the side wall of the bearing component 2.

At the point where the lower posterior groove 26 meets the upper anterior groove 27 there is an enlargement provided by a circular vertically extending well 32, the diameter of which is equal to the horizontal distance extending between the base of the groove on either side of the recess 23.

The posterior end of the upper groove 27 is closed by a wall 33.

The horizontal distance between the base of the grooves 26 and 27 and indicated by arrows 26a is slightly more than the diameter of the flange 17 on the boss 8, the vertical depth of the lower posterior groove 26 is slightly greater than the vertical thickness of the flange 17 and the vertical depth of the upper anterior groove 27 is slightly greater again.

FIGS. 5 to 10 show how the bearing component 2 is placed in position and located on the tibial tray 1.

Figure 5:
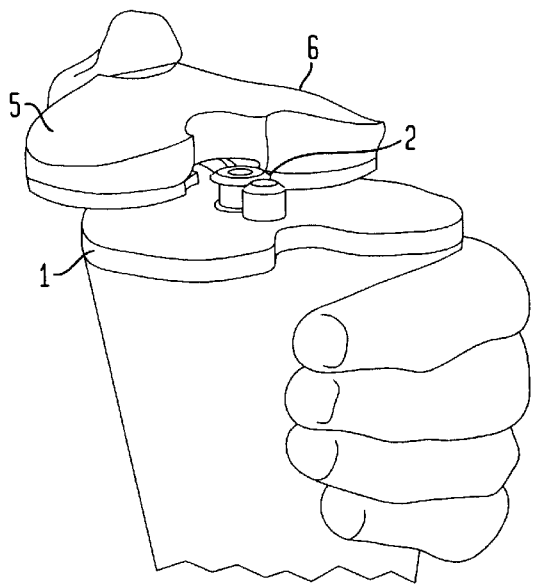
FIG. 5 is a diagrammatic representation showing how the bearing component is placed in position on the tibial tray.
Figure 6:
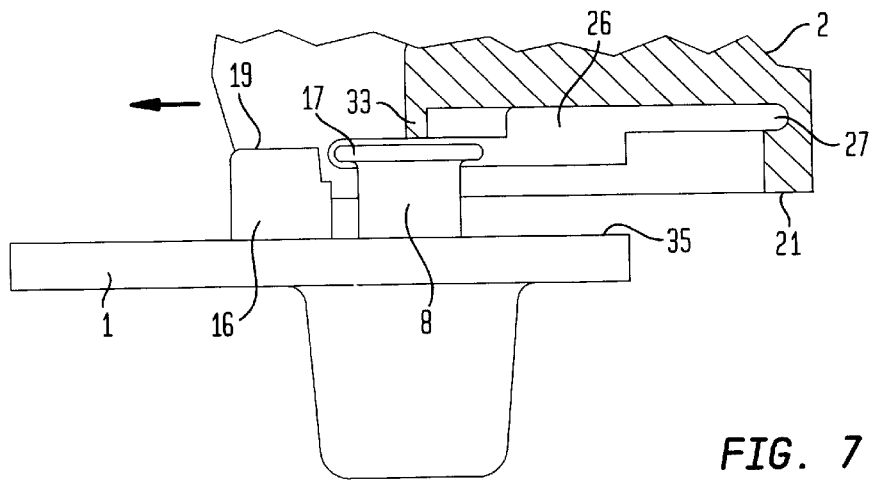
FIG. 6 is a part cross-sectional side view showing the bearing component in the position shown in FIG. 5 and about to be pushed into position.

In the position shown in FIGS. 5 and 6 the bearing component is inserted by pushing its posterior side towards the boss 8. At this position, as shown in FIG. 6, the lower surface 21 of the bearing component is raised above the upper surface 35 of the tray so that the open ends 31 of the lower posterior groove 26 engage over the flange 17 of the boss 8.

Figure 7:
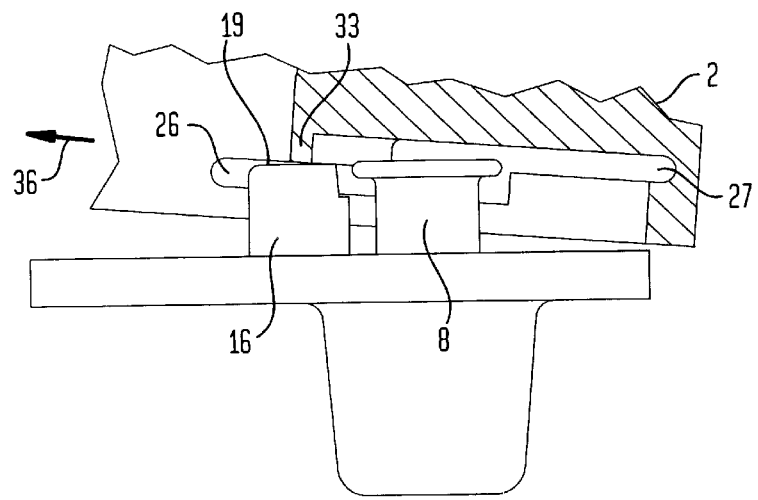
FIGS. 7 and 8 are views similar to FIG. 6 showing the bearing component in sequential loading positions of assembly.

Further movement in the direction of the arrow 36 in FIG. 7 shows that the bearing component 2 now has to be tipped to allow the flange 17 on the boss 8 to pass upwardly through the well 32 and into the upper anterior groove 27. The tipping movement is caused due to the upper surface 19 of the abutment 16 engaging the wall 33 at the end of the upper groove 28, and the flange 17 passing upwards in the well 32.

Figure 8:
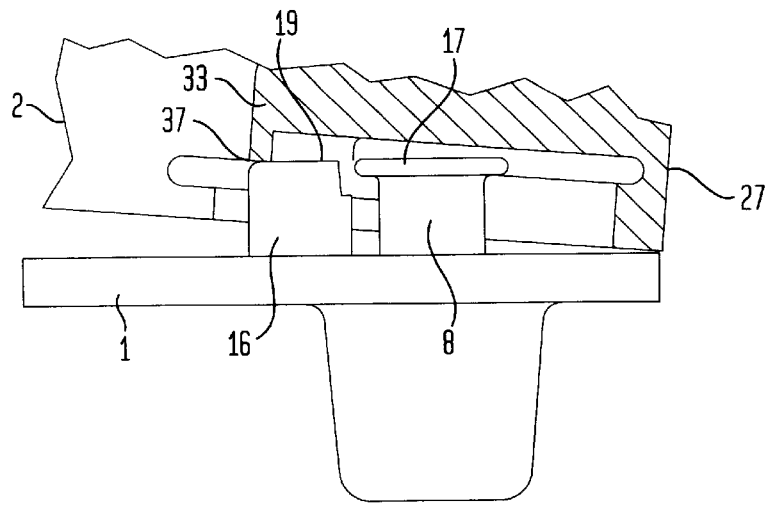

Further posterior movement achieves the position shown in FIG. 8 in which the anterior side of the flange 17 of the boss 8 has entered the upper groove 27, but the posterior corner 37 is still engaging the lower corner of the wall 33.

Figure 9:
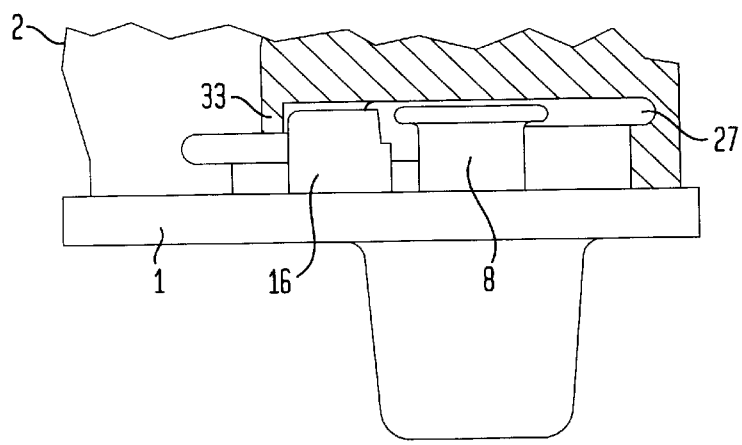
FIG. 9 is a view similar to FIG. 6 showing the bearing component after loading and in an anterior position.

Due to the resilient nature of the material from which the bearing component is made, UHMWPE, the bearing component can now be snapped downwards by resiliently deforming the end of the wall 3 over the corner 37 of the abutment 16 to the position shown in FIG. 9 where the bearing component is in its most anterior position. It will be seen that the abutment 16 now engages within the curved portion 29 at the posterior end of the upper groove 27 and the wall 33 prevents further anterior movement.

Figure 10:
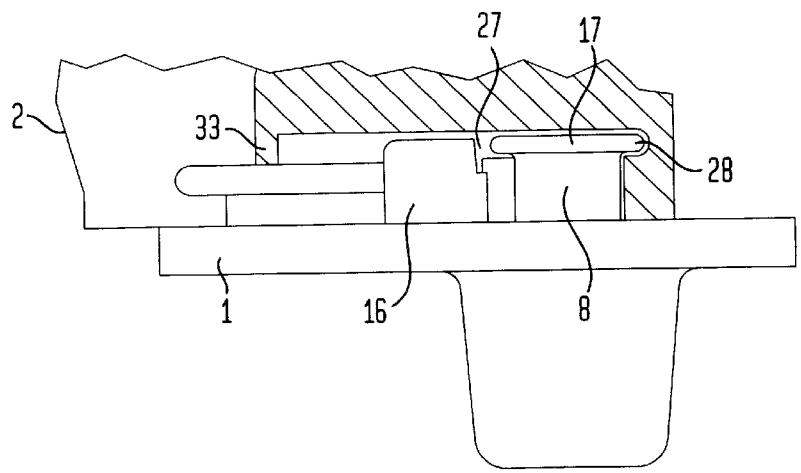
FIG. 10 is a view similar to FIG. 9 showing the bearing component after loading and in a posterior position.

The bearing component can, however, move in a posterior direction until the boss 8 engages the anterior end of the recess 23 as shown in FIG. 10. The flange 17 acting in the upper groove 27 prevents vertical removal of the bearing component and its horizontal movement on the tray 1 is controlled by the guide abutment 16 and boss 8 which are located in tandem in the curved track 22.

Thus, the boss 8 provides a guide and with its flange 17 provides independently operable means for securing the bearing to the tray, the bearing component being a resilient snap fit into the guide that can be releasable.

The abutment 16 and boss 8 which are in tandem together act as control means between the tray and the bearing component to allow free posterior and anterior movement of the lateral compartment 4 which is greater than the small amount of free posterior and anterior movement of the medial compartment 3 in relation to the tray 1.

Figure 11:
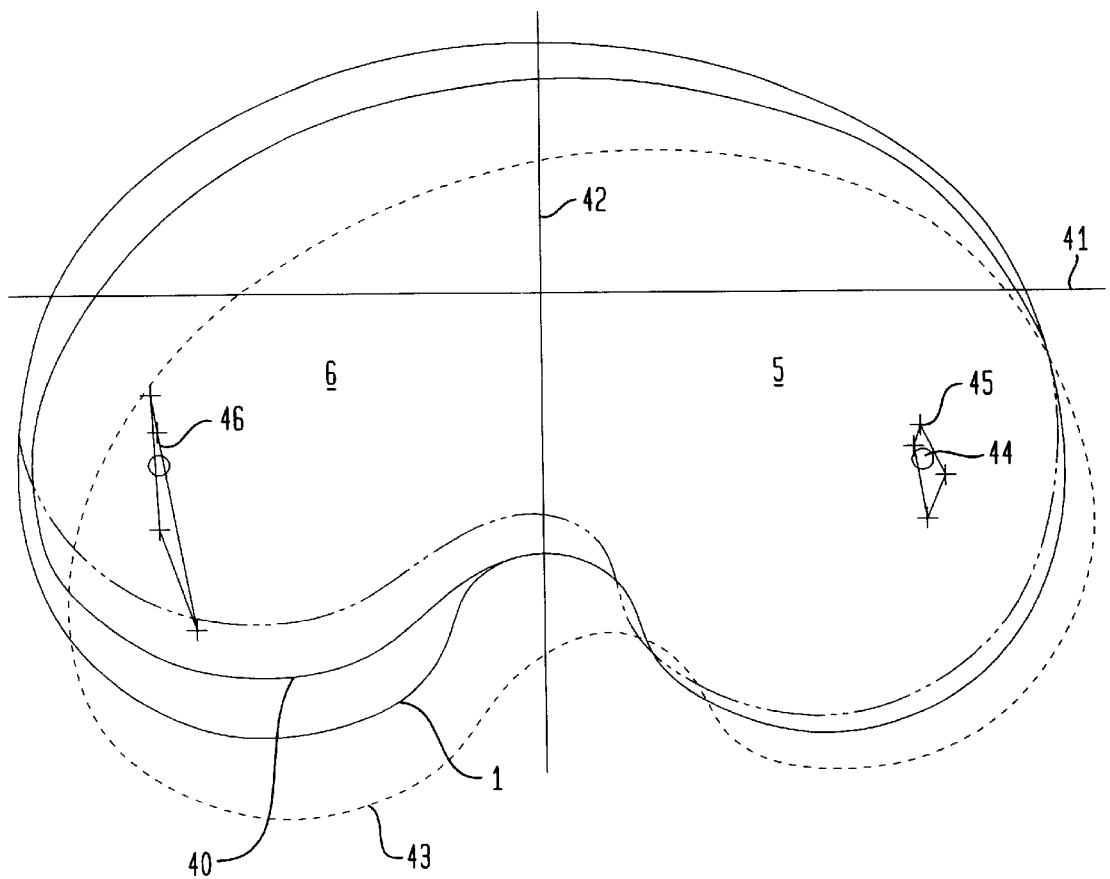
FIG. 11 is a diagrammatic plan view illustrating the range of movement of the bearing component on the tray.

FIG. 11 shows the relative movement. The central position of the bearing component 2 on the tray 1 is indicated by solid line 40. The general axes of the tray 1 are indicated by broken lines 41 and 42. From this it will be seen that in plan view the tray 1 is symmetrical about the center line 42 but the medial compartment 5 of the bearing component 2 is larger than the tibial compartment 6.

From this central position the maximum posterior movement of the bearing component is indicated by broken line 43 and it will be seen that the tibial compartment has rotated about a mobile axis 44, the locus of the movement of which is indicated by the lines and crosses 45. The locus of movement of a similar point on the lateral compartment 6 is indicated by crosses and lines 46 and the much greater range of movement will be apparent.

If desired, the shape of the track 22 can be arranged so that there is virtually no relative free posterior movement and anterior movement of the medial compartment 5.

In the construction described and shown in the drawings the control means acting between the tray 1 and the bearing compartment 2 allow rotational movement of the lateral compartment 6 in relation to the tray 1 about the pivotal axis 44 centered on the medial compartment and the arrangement allows restricted anterior and posterior movement of this pivotal axis.

It will be appreciated that other means for controlling the movement of the lateral compartment could be employed, for example, the control means could be in the form of a pivot which provides an axis of rotation and which would be centered on the medial compartment. Such a pivot could even allow a restricted free posterior and anterior movement relative to the tray.

Figure 12:
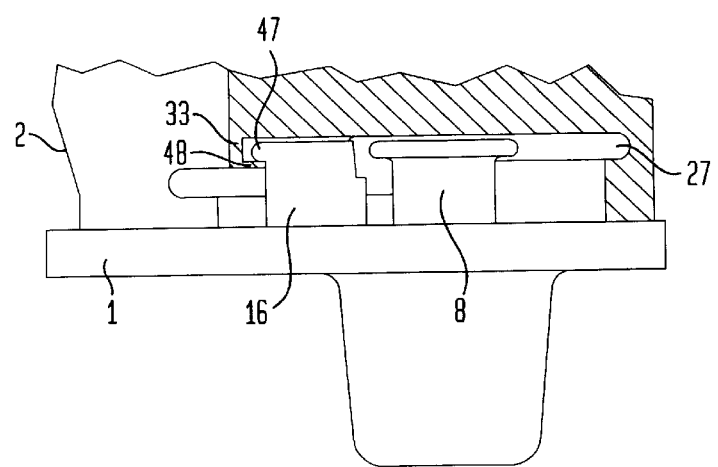
FIG. 12 is a view similar to FIG. 9 but showing a construction in which the bearing component is not removable.

FIG. 12 shows an alternate construction in which the bearing component 2 is not removable once it has been fitted. In this construction the abutment 16 is provided with a projecting lip 47 which can engage a cooperating lip 48 on the wall 3 to prevent the bearing component 2 from being tipped to allow the wall 33 to be resiliently deformed and sprung over the corner 37 of the abutment 16.

Figure 13:
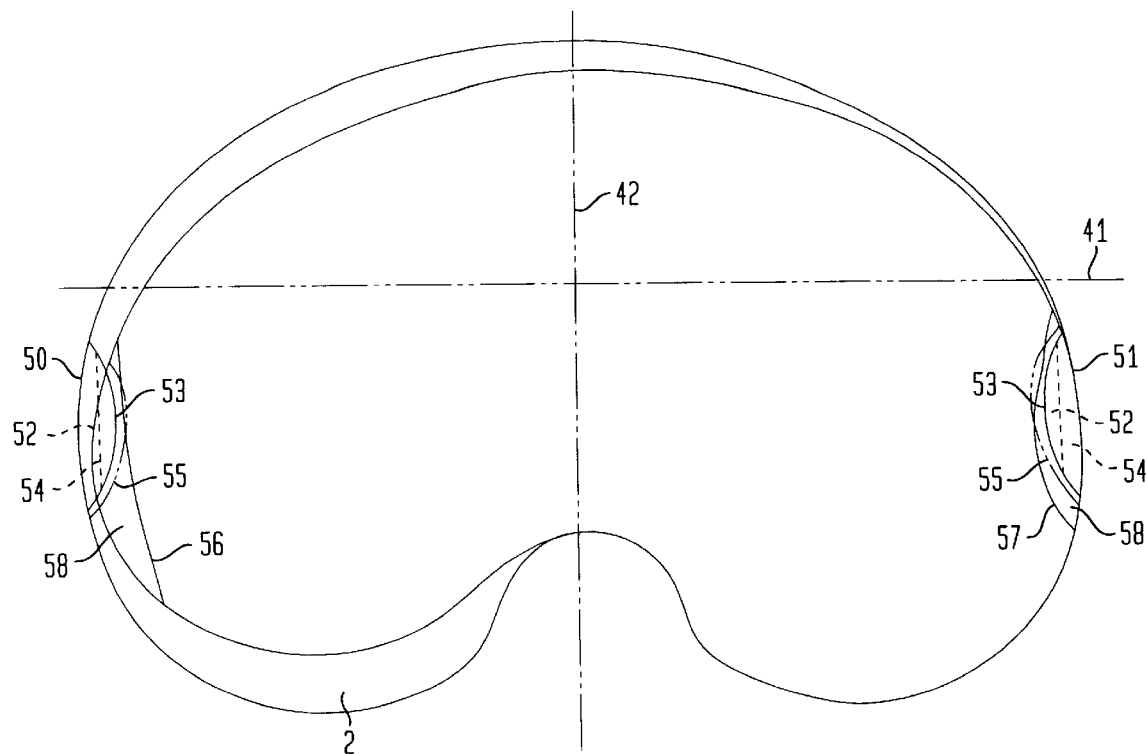
FIG. 13 is a diagrammatic plan view of the bearing component in position on the tibial tray and showing additional features which can be incorporated.

FIG. 13 shows a construction in which a multi-functional tibial tray is employed and which can be used for a construction as described above and as shown in the drawings or with one in which the bearing component is fixed in position in relation to the tray 1.

With this construction, medial and lateral retaining means are provided in the form of abutments 50 and 51. Each abutment comprises an upwardly projecting portion 52 and a horizontally projecting flange 53. The bearing component for use in this construction has an outwardly projecting flange 54 enclosed in a cut out segment 55 indicated by broken lines. The construction is such that as the bearing component is snapped into position the flanges 54 resiliently deform and pass below the flanges 53 so that the edges of each segment, 55 locate the bearing component against posterior and anterior movement.

When such a tray is to be used with a sliding meniscal component of the kind described herein and with reference to the drawings, the bearing component is cut away on each side along a line indicated by reference numerals 56 and 57 so that the relative movement between the tray and the bearing component is not impaired.

It will be appreciated that with the constructions described above in which the bearing component moves in relation to the tray that the bearing components have to be handed.

Figure 14:
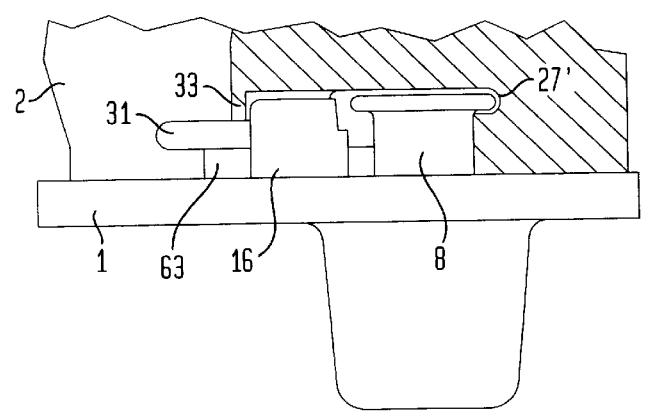
FIG. 14 is a view similar to FIG. 9 showing another alternate construction in which the bearing component is fixed in relation to the tray.
Figure 15:
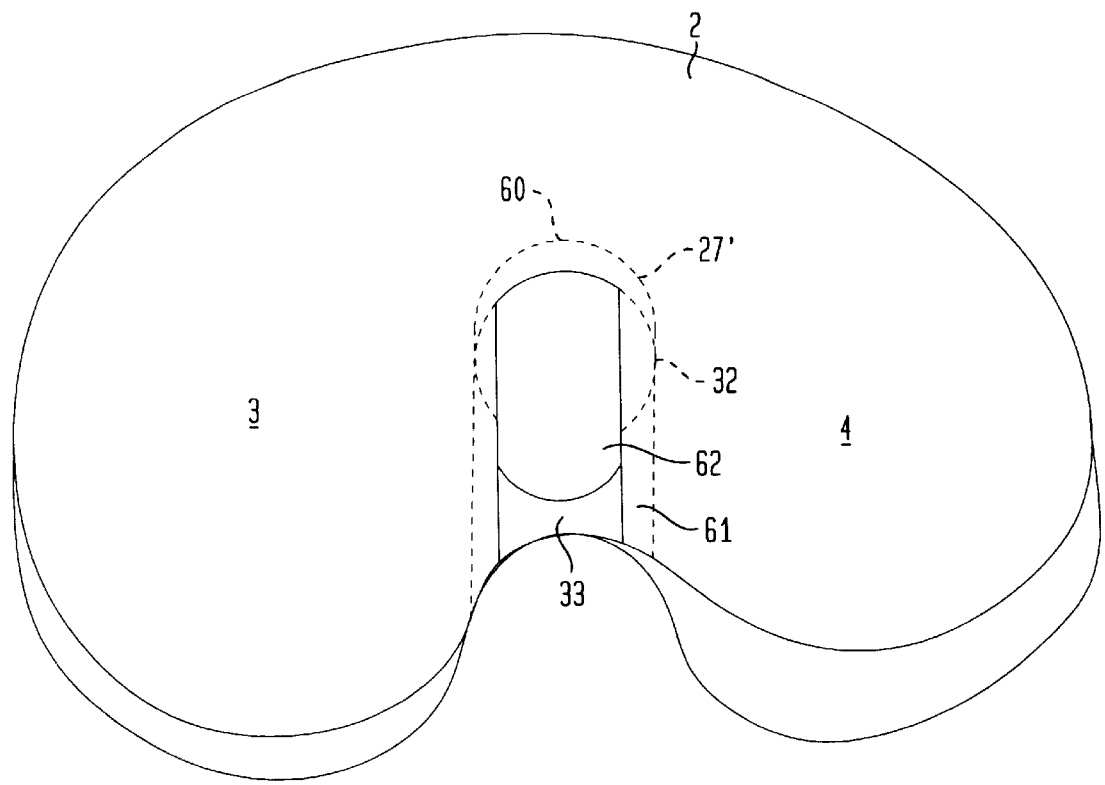
FIG. 15 is a view similar to FIG. 4 showing a tray for use with the bearing component shown in FIG. 14.

FIGS. 14 and 15 show a construction in which the bearing component 2 is not movable in relation to the tray 1 once it has been secured in position. Similar reference numerals are used to indicate similar parts to those described with regard to the preceding constructions.

In this fixed arrangement the upper groove 27, is considerably shortened so that its anterior end 60 extends merely as an extended groove surrounding the upper end of the well 32. Thus, the well now has a surrounding groove at each side and at its anterior side, this groove terminating at each side in the wall 33.

The curved track 22 is replaced by a straight track 61 and a straight recess 62. The securing flange 24 of the previous constructions is, of course, now straight and is indicated by reference numeral 63.

With this construction the bearing component 2 is fitted in a similar way to that described with regard to FIGS. 6 to 8 but the shortened upper groove 27, ensures that the position on the tray 1 is fixed. Moreover, due to the straight guide track 61 there is no sideways movement, the abutment 16 acting posteriorly of the boss 8 against the sides of the straight securing flange 63.

With this arrangement the bearing component 2 can be removed if desired in a similar manner to that described with regard to the removal of the bearing component in the construction shown in FIGS. 1 to 11.

If it is intended that the bearing component should be fixed and non-removable then a projecting lip can be provided on the abutment 16 to engage a cooperating lip 48 on the wall 33 in a similar manner to that described with regard to FIG. 12.

Figure 16:
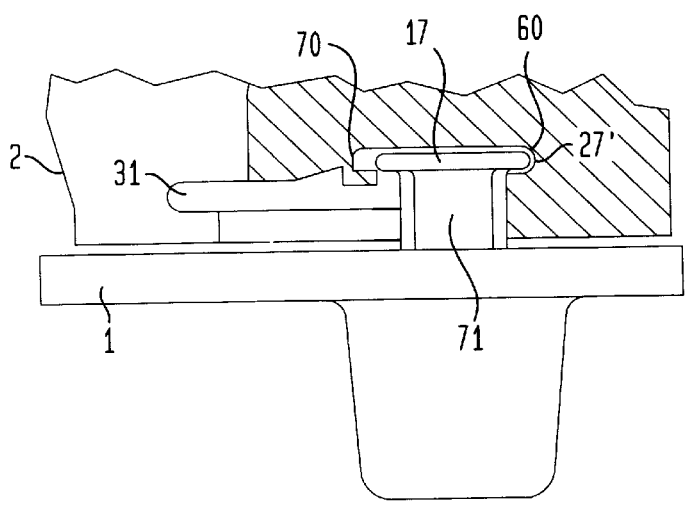
FIG. 16 is a view similar to FIG. 9 showing another alternate construction in which the position of the bearing component is fixed.
Figure 17:
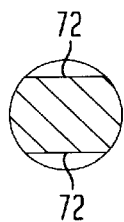
FIG. 17 is a cross-sectional view through the boss shaped head of the screw that retains the stem and for use in the construction shown in FIG. 16.

FIGS. 16 and 17 show an alternate construction for use when there is no requirement for relative movement between the bearing component and the tray 1. The same reference numerals are used to indicate similar parts to those described with regard to the other figures. In this arrangement, a straight track 61 and straight recess 62 are again employed and the anterior end 60 of the groove is again shortened and is similar to the construction shown in FIGS. 14 and 15. The posterior end of the upper groove 27, is also shortened so that the upper groove is effectively circular and the wall 33 is replaced by a deformable retaining wall 70.

The abutment 16 is deleted from the tray 1 and the boss 71 is provided with flats 72 on its opposed sides. This portion of the boss 71 could be replaced by a collar carrying the flats and which, when the screw 7 was tightly engaged into the stem, hold the collar in a fixed posterior anterior position.

The bearing component 2 is again loaded into a position in a similar manner to that described with regard to the preceding constructions but once it is in position in the well 32, the flats on its sides engage the sides of the track 61 and prevent rotation of the bearing component. The location of the flange 17 in the modified groove 27, prevents upward removal of the bearing component and due to the groove 27, being substantially circular movement in all directions is prevented.

The bearing component 2 can be removed in a similar manner to the constructions described above. If, however, it is intended that the bearing component should be unremovable, then at the lower end of the wall 70 a lip, similar to the lip 48 shown in FIG. 12, can be provided which engages beneath the flange 17 preventing removal.

In all the constructions shown in FIGS. 14 to 16 the tray 1 and bearing component 2 can also be provided with medial and lateral retaining means as described with regard to FIG. 13.

Figure 18:
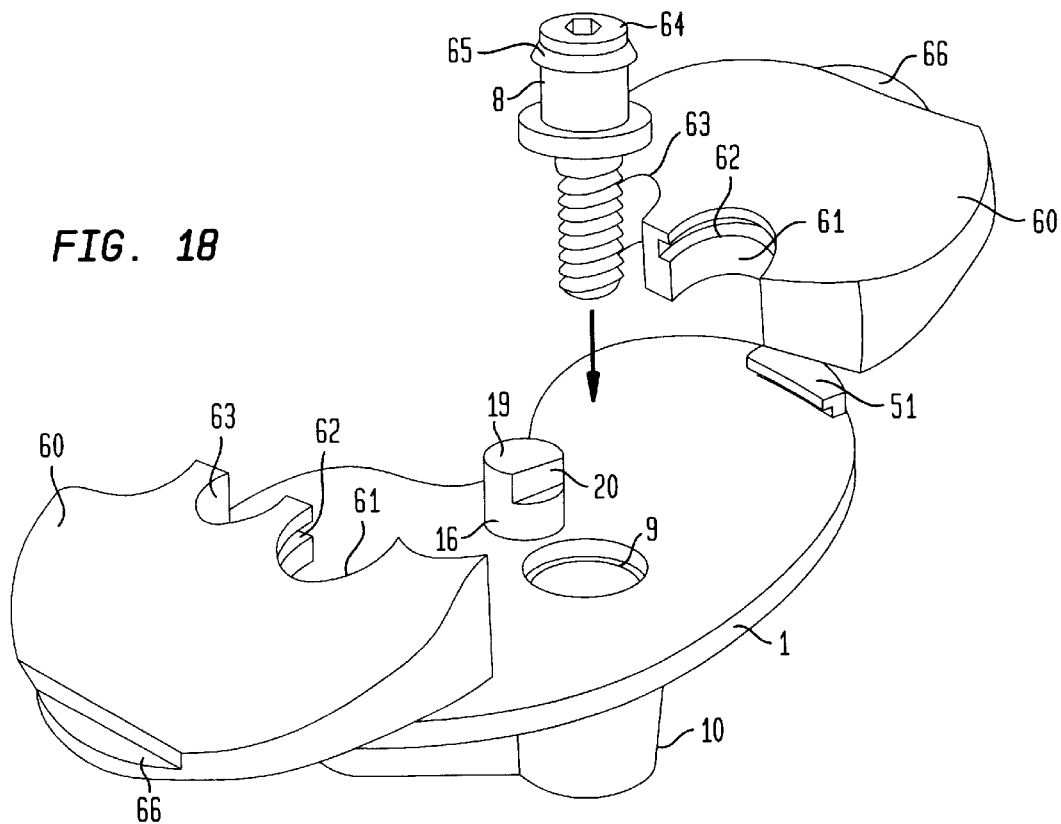
FIG. 18 shows an alternate construction using two bearing components.

FIG. 18 shows an alternate construction in which two bearing components are employed. With this arrangement the tray has an upper configuration similar to that shown in FIG. 13 of the previous embodiments, that is it is provided with abutments 50 and 51. Each of the bearing components 60 is provided with a re-entrant portion 61 which carries a groove 62. A second re-entrant portion 63 is also provided to encompass the abutment 16 when the bearing component is in position.

A screw 64 acts to hold the stem 11 (not shown in FIG. 18) in place and this screw 64 is formed with a boss shaped head 8 above which is projecting tapered flange 65.

With the screw 64 in place outwardly projecting flanges 66 provided on the bearing components are first pushed into place beneath the abutments 50, 51 and are then snapped downwards so that the grooves 62 snap into place beneath the tapered flange 65. The bearing components are further located by the abutment 16.

In order to remove the bearing components, it is merely necessary to insert a spatula beneath the components and between them and the tray 1 and to lever upwards so that the groove 62 snaps out of position on the tapered flange 65.

Figure 19:
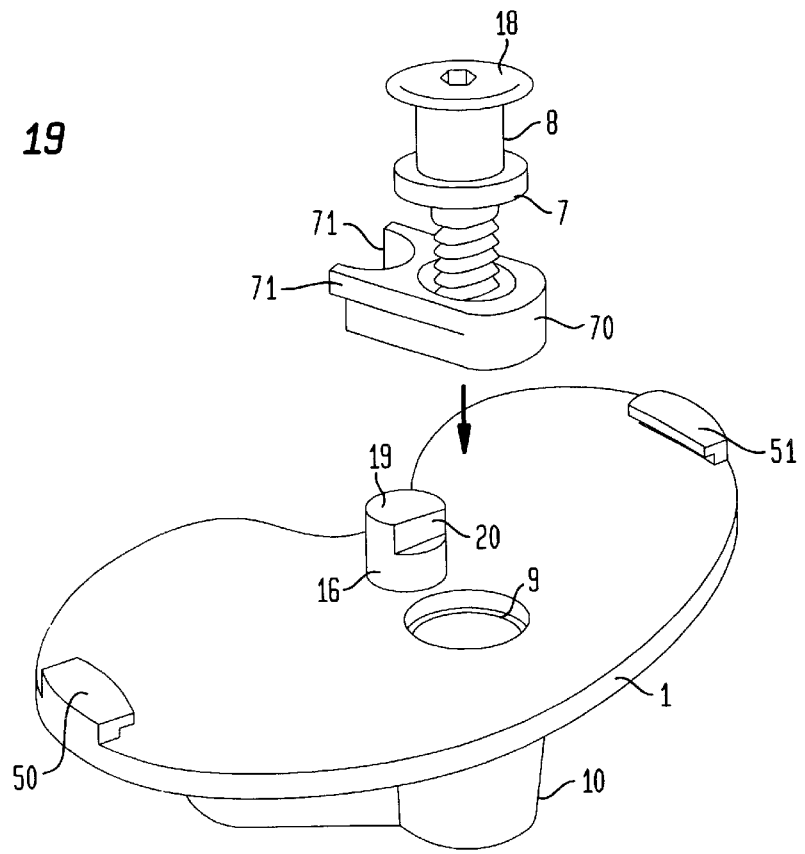
FIG. 19 shows another alternate construction for use with two bearing components.

FIG. 19 shows another alternative construction in which a screw 7 similar to that used in previous embodiments is employed but in this case the screw locates a location member 70 which is undercut on its lower side to provide projecting flanges 71 on each side. The general construction of the tray 1 is similar to that described with regard to FIG. 18 and two bearing components 60, again similar to that shown in FIG. 18, can be used. In this construction however, the ends of the bearing components are not provided with the re-entrant portions 61 but have a straight corner edge which snaps under the appropriate flange 71 on the retaining member 70.

In all the above constructions the bearing components can be made of any suitable material for example, ultra high molecular weight polyethylene and the tray and stem can be formed from, for example, stainless steel.

We claim:

1. A tibial element for a replacement knee prosthesis comprising a tibial tray having an upper surface, a fastener extending through said tray for securing a stem to the lower part of said tray, said fastener provided with a flanged securing post at its upper end; a stop post extending from said upper surface spaced from said securing post; a bearing component having a groove formed on the underside of said bearing component for engaging a flange on said flanged securing post to secure the bearing component to the upper surface of said tray; and said groove having an upper section and a lower section with said lower section having an open posterior end.

2. A tibial element as claimed in claim 1 in which said bearing component can slide in relation to the tray when secured.

3. A tibial element as claimed in claim 2 in which said fastener acts as a guide between the tray and the groove on said bearing component for controlling sliding movement of the bearing component in relation to the tray.

4. A tibial element as claimed in claim 3 in which said groove includes a curved track formed in a base of the bearing component.

5. A tibial element as claimed in claim 4 wherein said groove has a T-shaped cross-section with the T portion receiving said flange on said securing post.

6. A tibial element as claimed in claim 1 in which said post is provided with a boss at its upper end which is shaped to cooperate with the groove on the bearing component.

7. A tibial component for a knee prosthesis comprising:

a tibial tray having a generally flat upper surface;

a first post extending outwardly from said upper surface, said post having a flange at an upper end, said flange extending in a direction generally parallel to said upper surface;

a second post located posteriorly of said first post; and a bearing insert having at least one condyle formed on an upper surface thereof and two recessed grooves formed on a bottom surface thereof, said bottom surface slidably engaging said upper surface of said tibial tray, said grooves being spaced from one another in a direction extending between said bottom and upper surfaces of said insert forming upper and lower grooves with an opening for said flange connecting said grooves, said lower groove adjacent said bottom surface being open in the posterior direction when assembled with said flange of said first post engaging said upper groove.

8. The tibial component as set forth in claim 7 wherein at least one of said grooves forms a curved track.

9. A tibial element for a replacement knee prosthesis comprising a tibial tray having an upper surface and a lower part, a fastener extending through said tray for securing a stem to the lower part of said tray, said fastener provided with a flanged securing post at its upper end; and a pair of bearing components, each having a groove formed on an underside of said bearing component for engaging a flange on said flanged securing post to secure the bearing component to the upper surface of said tray.

10. A tibial element as claimed in claim 9 in which each bearing component is independently engageable with the flanged post.

11. A tibial element as claimed in claim 10 in which the tray is substantially symmetrical about a vertical axis.

12. A tibial element for a replacement knee prosthesis comprising a tibial tray having an upper surface, a fastener extending through said tray for securing a stem to a lower part of said tray, said fastener provided with a flanged securing post at its upper end; a stop post extending from said upper surface spaced from said securing post; a bearing component having two vertically spaced apart grooves on an underside of said bearing component for engaging a flange on said flanged securing post to secure the bearing component to the upper surface of said tray; an upper groove of said grooves forming a securing flange in the bearing component and the grooves being interconnected to allow the flange on the post to move between them; and a lower groove of said grooves having an open posterior end for receiving said flange and said post shaped to engage said securing flange on said grooves.

* * * * *

UNITED STATES PATENT AND TRADEMARK OFFICE
CERTIFICATE OF CORRECTION

PATENT NO. : 5,928,286
DATED : July 27, 1999
INVENTOR(S) : Ashby et al.

It is certified that error appears in the above-identified patent and that said Letters Patent is hereby corrected as shown below:

Column 5, line 46, "27," should read -- 27' --.
Column 5, line 59, "27," should read -- 27' --.
Column 6, line 14, "27," should read -- 27' --.
Column 6, line 28, "27," should read -- 27' --.
Column 6, line 29, "27," should read -- 27' --.

Signed and Sealed this

Seventh Day of November, 2000

Attest:

Q. TODD DICKINSON

*Attesting Officer*    *Director of Patents and Trademarks*